(12) United States Patent
Green et al.

(10) Patent No.: US 8,992,607 B2
(45) Date of Patent: Mar. 31, 2015

(54) PROSTHETIC ANATOMICAL DEVICE WITH SEWING CUFF FLANGE AND ANTI-ROTATION FEATURE

(71) Applicant: St. Jude Medical, Cardiology Division, Inc., St. Paul, MN (US)

(72) Inventors: Chad Joshua Green, Forest Lake, MN (US); Grant Tsuchiya, Minnetonka, MN (US); Mindy Lor, St. Paul, MN (US); Bruce Roman Musolf, Eagan, MN (US); Zhengrong Zhou, Shanghai (CN); Gary Fischbach, Albertville, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 13/782,314

(22) Filed: Mar. 1, 2013

(65) Prior Publication Data

US 2014/0114409 A1    Apr. 24, 2014

Related U.S. Application Data

(60) Provisional application No. 61/717,882, filed on Oct. 24, 2012.

(51) Int. Cl.
*A61F 2/24*    (2006.01)

(52) U.S. Cl.
CPC ....... *A61F 2/2448* (2013.01); *A61F 2220/0008* (2013.01)
USPC ........ 623/2.37; 623/2.36; 623/2.38; 623/2.39

(58) Field of Classification Search
CPC ............................ A61F 2/2448; A61F 2/2445
USPC ................................................ 623/2.36–2.42
See application file for complete search history.

(56) References Cited

U.S. PATENT DOCUMENTS

| 3,800,403 | A  | * | 4/1974  | Anderson et al. ................ 29/445 |
| 6,790,226 | B2 | * | 9/2004  | Edwin et al. .................. 623/1.13 |
| 2005/0256567 | A1 | * | 11/2005 | Lim et al. ...................... 623/2.36 |
| 2010/0030329 | A1 | * | 2/2010  | Frater .......................... 623/2.36 |
| 2011/0238170 | A1 | * | 9/2011  | Lim et al. ...................... 623/2.36 |
| 2012/0022643 | A1 | * | 1/2012  | Vanermen et al. ............ 623/2.36 |
| 2012/0136435 | A1 | * | 5/2012  | Brunnett et al. ............. 623/2.36 |

* cited by examiner

*Primary Examiner* — Jason-Dennis Stewart
(74) *Attorney, Agent, or Firm* — Lerner, David, Littenberg, Krumholz & Mentlik, LLP (57) ABSTRACT

A prosthetic anatomical device, such as, for example an annuloplasty prosthesis, is disclosed in which the prosthesis comprises a generally annular core and a cover surrounding the core, with at least a portion of the cover forming a cuff. In some embodiments, the cover may be particularly configured about the core to form the cuff. Various methods and structures for mitigating or retarding movement between the annular core and the fabric cover are also disclosed.

31 Claims, 5 Drawing Sheets

PROSTHETIC ANATOMICAL DEVICE WITH SEWING CUFF FLANGE AND ANTI-ROTATION FEATURE

CROSS-REFERENCE TO RELATED APPLICATIONS

This application claims the benefit of the filing date of U.S. Provisional Patent Application No. 61/717,882 filed Oct. 24, 2012, the disclosure of which is hereby incorporated herein by reference.

BACKGROUND OF THE INVENTION

The present invention relates, in general, to embodiments of a prosthetic anatomical device having a particularly designed sewing cuff. Methods and structures for securing the cuff to the prosthetic anatomical device, such that rotational stability is achieved therebetween, are also disclosed.

Typically, prosthetic anatomical devices, such as, for example, annuloplasty prostheses, include a core member that in some cases may be surrounded by a soft fabric cover. The core member is often substantially rigid or at least semi-rigid and is not penetrable by a suture needle and suture material. The fabric cover may be designed to cushion the prosthesis, and possibly also to promote tissue in-growth into the prosthesis to help integrate the prosthesis into the patient's body. It is often desired to secure the prosthesis to the patient by passing one or more suture needles and suture material through the fabric cover and adjacent tissue. Tightness and/or thinness of the fabric cover may, however, make this difficult to do. For example, a tight and/or thin fabric cover may result in a surgeon accidentally threading a needle through the core member, which can result in damage to the ring and/or needle. What's more, even if the surgeon is successful in getting proper engagement between the needle and the fabric cover, the amount of fabric caught may be less than would be desirable for good tissue healing and/or over-growth.

To facilitate suturing an annuloplasty prosthesis to a patient, a sewing cuff may be provided with the prosthesis. Examples of a sewing cuff(s) used for this purpose are found in at least U.S. Pat. No. 7,938,856 to Lim et al. ("Lim"), which is incorporated by reference herein in its entirety. These sewing cuffs are generally extensions of the fabric cover that is provided around the core of the prosthesis, which supplies a surgeon with an area to anchor the annuloplasty prosthesis and allow for tissue in-growth at the surgical site. Further, in the case of Lim, since the cuff typically extends from the core member, the surgeon is provided with an area to secure the ring to the patient, which is not adjacent to or near the core member. As such, the surgeon is less prone to inadvertently contacting the core member while suturing the cuff to the patient. In addition, the cuff also allows a surgeon the ability to position and hold the annuloplasty ring in a desired orientation within the valve annulus (e.g., by suturing the cuff and therefore the prosthesis to the patient in a particular orientation).

Figure 6:
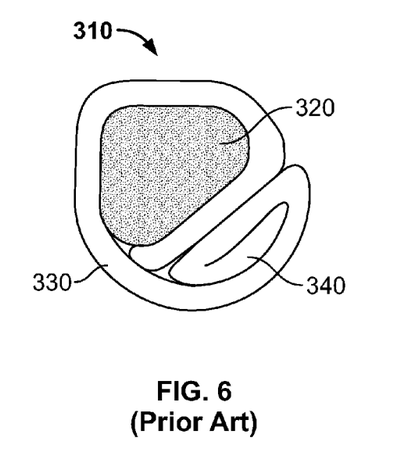
FIG. 6 is a cross-sectional view of a prior art annuloplasty prosthesis.

An alternate version sewing cuff is shown in FIG. 6 in which the cuff 340 is formed by wrapping a cover 330 about a core 320 of prosthesis 310. Here, the portion of cover 330 forming cuff 340 is folded over on itself, and is generally situated against or close to the core 320 of prosthesis 310, as opposed to extending outward therefrom. Prosthesis 310, with this specifically designed cover 330 forming cuff 340, is currently sold by St. Jude Medical® under the trade name "Rigid Saddle Ring with EZ Suture™ Cuff."

Annuloplasty prostheses with a cuff, as described, can experience rotational instability relative to the core of the prosthesis. Stated differently, in some cases, the fabric forming the cuff is able to rotate relative to the prosthesis core, causing the desired orientation of the prosthesis to change. This may have the effect of changing the shape of the opening created by the prosthesis, as many prostheses have a D-shaped profile or, in some cases, a C-shaped profile. Alternatively, such rotational instability may make it more difficult for the surgeon to suture the prosthesis to a patient, which is primarily due to unwanted movement of the fabric cover with respect to the core.

BRIEF SUMMARY OF THE INVENTION

A first aspect of the present invention includes a prosthetic anatomical device comprising an annular core and a cover at least partially surrounding the core and forming a cuff extending radially outward from the core, the cover formed from a material layer having a first section folded at least once over itself and a second section folded at least once over itself, with a portion of the second section forming the cuff.

In embodiments of this first aspect, the second section is at least twice folded over itself, and the first section is stitched to the second section. Also, in some cases a polymer layer is situated between the annular core and the cover, whereby rotation between the cover and the core is reduced. The annular core may also comprise an annuloplasty ring.

A second aspect of the present invention includes a prosthetic anatomical device comprising an annular core with an outer surface, and a cover at least partially surrounding the core and having at least one section forming a cuff for suturing the cover to tissue within a patient, the cuff extending radially outward from the core. This second aspect may also include means for mitigating movement between the annular core and the cover.

In certain instances of the second aspect, the means may be a slip-resistant material arranged between the annular core and the cover. Various other means may also be utilized, as detailed below.

In a third aspect of the invention, a method of manufacturing a prosthetic anatomical device is set forth, the method comprising the steps of providing a prosthetic anatomical device having an annular core with an outer surface, and covering the outer surface of the annular core with a cover having at least one section forming a cuff for suturing the cover to tissue within a patient, the cuff extending radially outward from the core. The method according to this third aspect may also include a step of securing the annular core to the cover to mitigate movement therebetween.

In some embodiments of the third aspect, prior to the securing step, a slip-resistant material is situated between the outer surface of the annular core and an inner surface of the cover. In other cases, the securing step includes forming a stitch pattern into the cover to secure the cover about the core.

BRIEF DESCRIPTION OF THE DRAWINGS

A more complete appreciation of the subject matter of the present invention(s) and of the various advantages thereof can be realized by reference to the following detailed description in which reference is made to the accompanying drawings in which:

FIG. 7A is a perspective view of an alternate embodiment prosthetic anatomical device having a cross-stitch pattern, while

DETAILED DESCRIPTION

In describing the preferred embodiment(s) of the subject illustrated and to be described with respect to the drawings, specific terminology will be used for the sake of clarity. However, the invention(s) is not intended to be limited to any specific terms used herein, and it is to be understood that each specific term includes all technical equivalents, which operate in a similar manner to accomplish a similar purpose.

Annuloplasty prostheses for heart valves are well known, as shown, for example, in U.S. Pat. No. 6,726,717 to Alfieri et al., U.S. Pat. No. 6,805,710 to Bolling et al., and U.S. Pat. No. 7,297,150 to Cartledge et al. In some cases, such prostheses may be complete rings, or they may be less than complete rings (e.g., as disclosed in U.S. Pat. No. 3,656,185 to Carpentier). The term "annuloplasty ring" as used herein is intended to refer to both of these types of prostheses (i.e., both complete rings and less than complete annular structures).

Figure 1:
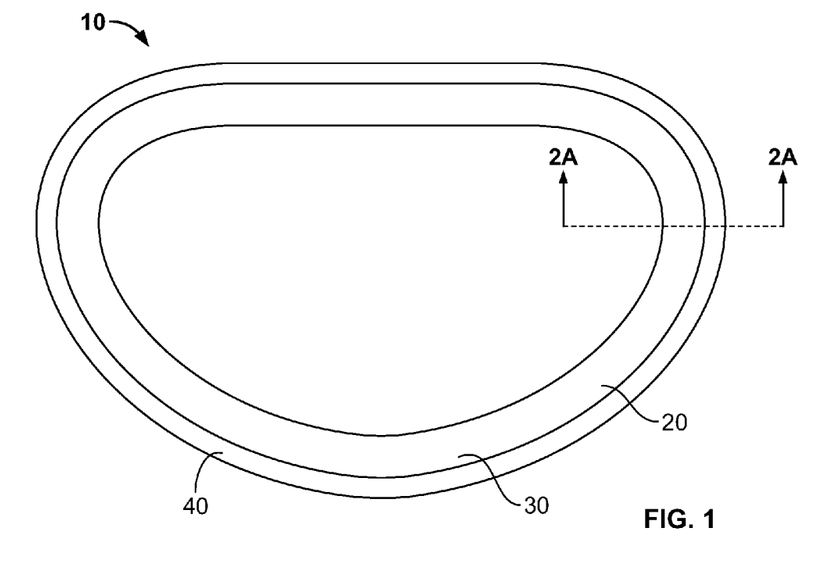
FIG. 1 is a plan view of a prosthetic anatomical device, such as, for example, an annuloplasty prosthesis, in accordance with one embodiment of the present invention.

FIG. 1 depicts an annuloplasty prosthesis or ring 10 (e.g., a mitral valve ring) having a core 20 surrounded by a fabric cover 30, a portion of which is configured to form a cuff 40. The cuff 40 extends radially outward from and around at least a portion of the periphery of the core 20, thus providing a surgeon with material for anchoring sutures (and therefore prosthesis 10) to tissue within a patient. In the preferred embodiment, the fabric cover 30 and/or cuff 40 extends completely about the periphery of the core 20.

Figure 2A:
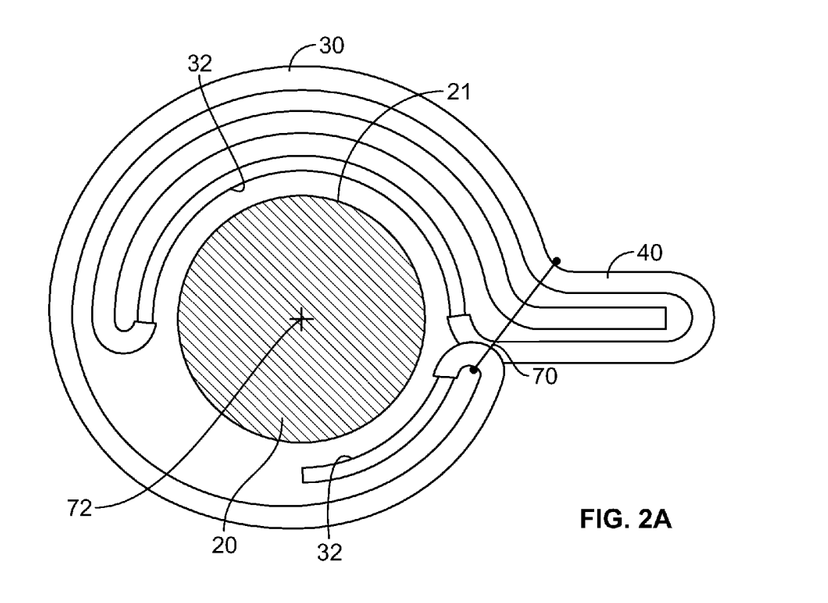
FIG. 2A is a cross-sectional view of the prosthesis of FIG. 1, taken along line 2A-2A thereof, in which a core member of the prosthesis is surrounded by fabric cover that is configured to form a cuff.

FIG. 2A depicts a cross-section of the annuloplasty prosthesis 10 of FIG. 1 in which the core 20 of prosthesis 10 is surrounded by the fabric cover 30, which is wrapped around core 20 to form the cuff 40. Fabric cover 30 may be a multi-layered cover, as shown, which consequently forms a multi-layered cuff 40. In particular, as shown in the unwrapped view of cover 30 in FIG. 2B, cover 30 may be a single layer of material 29 that is folded about itself at certain portions of the layer 29 to form multi-layered fabric cover 30. For example, at one section 33 of cover 30, the single layer 29 forming cover 30 may be folded about itself at least two (2) times, thereby forming a portion 33 of cover 30 having at least three (3) layers. Similarly, at an opposing section 34, the single layer forming fabric cover 30 may be folded about itself at least one (1) time, thereby creating a portion 34 of cover 30 having at least two (2) layers.

Figure 2B:
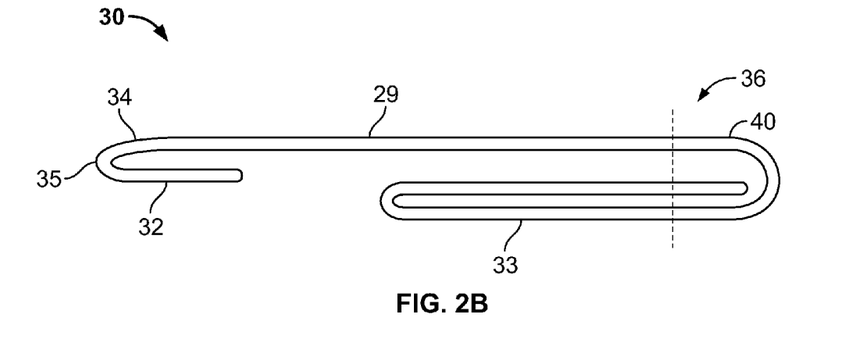
FIG. 2B is a view of the fabric cover of the prosthesis of FIG. 2A, in which the cover is unwrapped from the prosthesis.

These sections 33, 34 of fabric cover 30 may be wrapped about core 20 of prosthesis 10, as shown in FIG. 2A, such that an end 35 of cover 30 is situated adjacent a section of cover 30 represented by dotted line 36. Once wrapped in this manner, any amount of cover 30 extending to the right of dotted line 36, as shown in FIG. 2B, may be configured to form cuff 40. A suture or stitch 70 may thereafter be secured through the layers of cover 30 corresponding to sections 33, 34, as shown in FIG. 2A, through end 35 and at the location represented by dotted line 36.

Figure 2C:
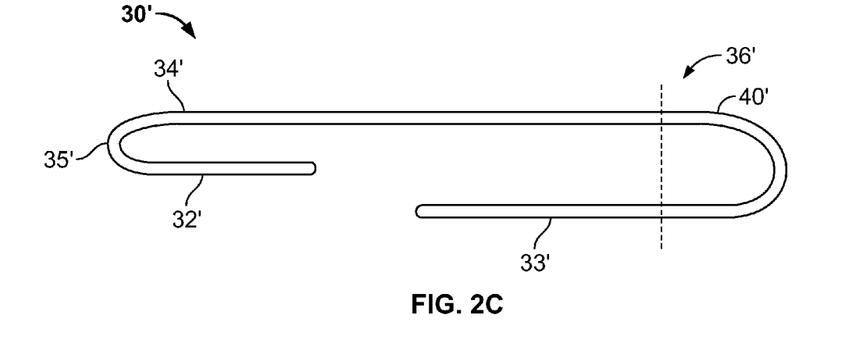
FIG. 2C is a view of an alternate embodiment of the fabric cover of FIG. 2B.

An alternate variant of the fabric cover of FIG. 2B is shown in FIG. 2C, in which a cover 30' is provided with a first section 33' being folded only once over, and a second section 34' being also folded only once over. Consequently, first and second sections 33', 34' of cover 30' may contain at least two (2) layers of material, as opposed to three (3) layers of material in section 33 of cover 30. Cover 30' may also be wrapped around the core 20 of prosthesis 10 in the same manner as cover 30; and specifically, around core 20, such that an end 35' of cover 30' is situated adjacent a section of cover 30' represented by dotted line 36'. The portions of cover 30' extending to the right of dotted line 36' may therefore be configured to form a cuff 40'. As with cover 30, a suture or stitch 70 may thereafter be secured through the layers of cover 30' corresponding to sections 33', 34'.

Referring now to FIGS. 2A-C, with FIG. 2A being exemplary, in one embodiment, only portions 32, 32' of the first layer of fabric cover 30, 30' may be secured to core 20; and the remainder of the layers of material forming cover 30, 30' may be wrapped around core 20 and portions 32, 32' so as to form cuff 40, 40'. A stitch 70 may thereafter be placed through the multiple layers of fabric cover 30, 30' corresponding to sections 33, 33' and 34, 34' so as to secure the cover 30, 30' together. Once so secured, cuff 40, 40' of fabric cover 30, 30' may extend outward from and perpendicular to a center axis 72 of the ring core 20 by some preferred amount, which, for example, may be about one (1) to three (3) millimeters. The suture or stitch 70 may be sewn in such a way that the same can be cinched tight, thereby pushing the cuff 40, 40' radially out from axis 72 and locking cuff 40, 40' into its final shape. In one embodiment, the stitch 70 may be a different color from the color of fabric cover 30, 30', so as to demarcate cuff 40, 40' from the rest of cover 30, 30'.

As thus far described, multi-layered cuffs 40, 40' of prosthesis 10 may provide a desired thickness for a surgeon or other skilled practitioner (hereinafter "the user") to insert sutures through. In other words, since multiple layers of fabric cover 30, 30' (e.g., at least two (2) in the case of FIG. 2C, and at least three (3) in the case of FIG. 2B) are used to form cuff 40, 40', as opposed to merely a single layer, the user may be provided with a thicker and improved cuff 40, 40' with which to thread a needle through.

Figure 3:
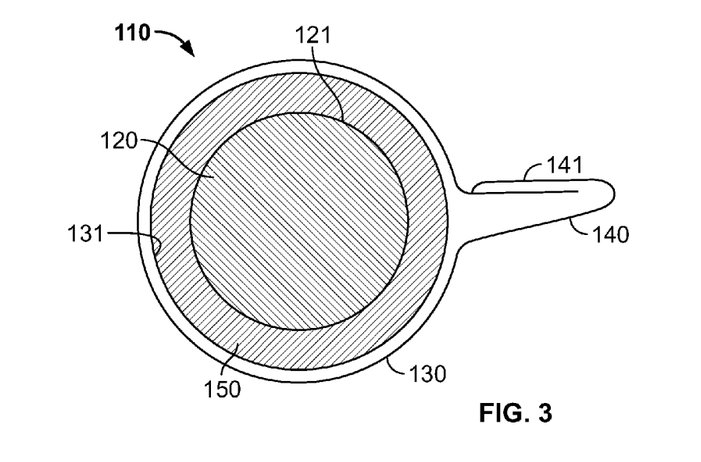
FIG. 3 is a cross-sectional view of an alternate embodiment of the prosthesis of FIG. 2A in which the core member is surrounded by a slip-resistant layer of material.

A cross-sectional view of an alternate version of prosthesis 10, designated as prosthesis 110, is shown in FIG. 3. There, a core 120 of prosthesis 110 is surrounded by a fabric cover 130 forming a cuff 140. As shown in this embodiment, fabric cover 130 may be a single layer of material that is wrapped around core 120 and is folded twice over on itself at one section 141 to form a cuff 140 having at least three (3) layers of material. A suture (not shown) may thereafter be placed at section 141 to secure the at least three layers (3) of cuff 140 to the rest of fabric cover 130.

Figures 4, 5A, 5B:
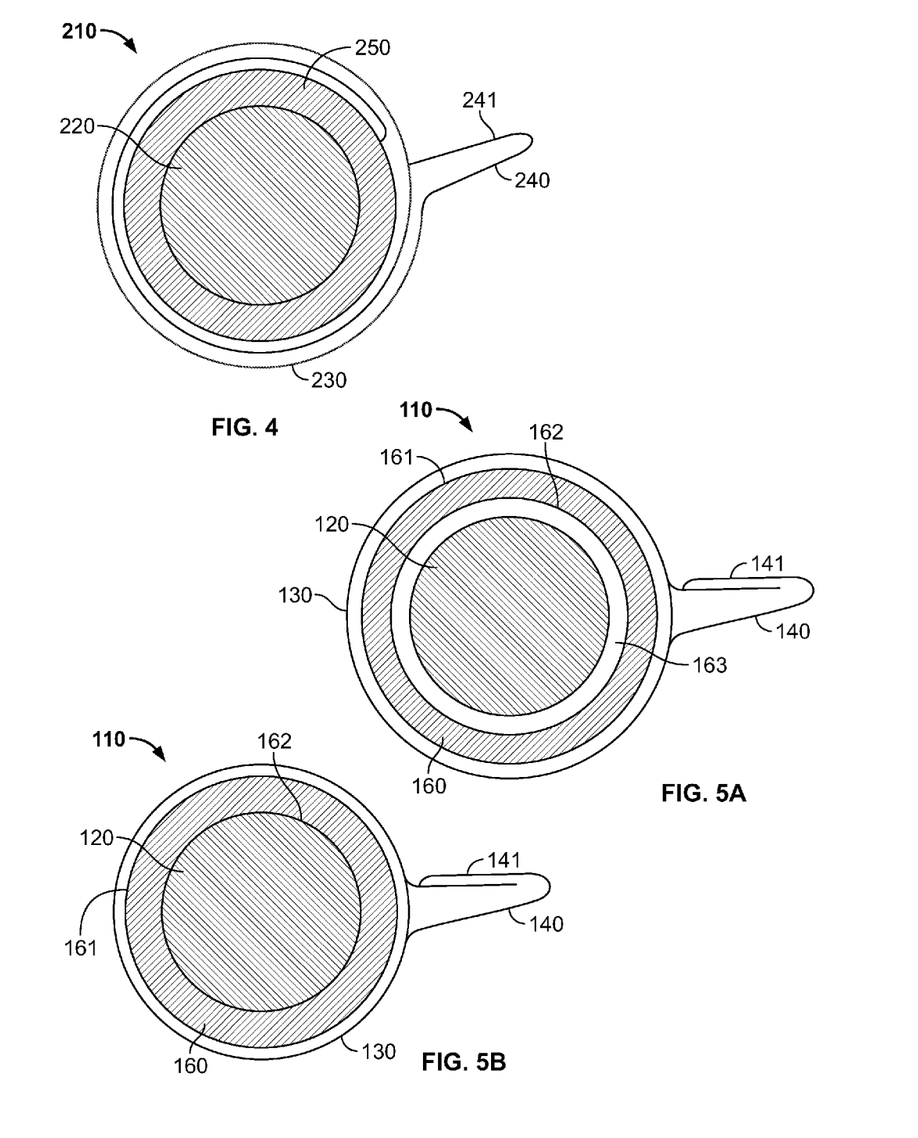
FIG. 4 is a cross-sectional view of an alternate embodiment of the prosthesis of FIG. 3 in which a fabric cover surrounding the core is specifically wrapped so as to form a cuff.
FIGS. 5A and 5B are cross-sectional views of another embodiment of the prosthesis of FIG. 3 in which the slip-resistant material is formed over the core member through a thermal shrinking process.

Referring now to FIG. 4, a further variant of prosthesis 10, designated as prosthesis 210, is shown. Prosthesis 210 includes a core 220 and a fabric cover 230 surrounding the core 220 and forming a cuff 240. Fabric cover 230 may be a single layer of material that is wrapped multiple times about core 220, and may be folded once over itself at section 241, as opposed to twice over itself as with prosthesis 110. Cuff 240 may therefore include at least two (2) layers of material. Once wrapped about core 220, cuff 240 may thereafter be secured to the rest of cover 230 via a suture (not shown), thus securing the multiple layers of section 241 of cuff 240 to fabric cover 230.

The present invention(s) further contemplates various embodiments providing for rotational stability between the core and fabric cover of any of prostheses 10, 110, 210, so as to maintain the proper orientation of the cuff relative to the core and provide a user with an improved suture cuff. These embodiments, as described below, generally may include, inter alia, the use of a slip-resistant material interposed between the core and fabric cover to provide friction therebetween. A stitch pattern is also used in one instance for ant-slip purposes. Primarily, the embodiments differ in the methods or processes in which the slip-resistant material is situated on and/or formed about the core of the prosthesis. While the use of a slip-resistant material in several embodiments is described in connection with prosthesis 110 embodied in FIG. 3, it is contemplated that any of the prostheses according to the other embodiments discussed (e.g., prosthesis 10, 210) may utilize the below-described slip-resistant materials and methods of forming the same.

In a particular embodiment, as shown in FIG. 3, a layer of slip-resistant material 150 may be formed on fabric cover 130. Specifically, slip-resistant material 150 may be formed on an interior surface 131 of fabric cover 130, which completely or at least partially surrounds core 120, and material 150 may not be present within the cuff 140 of fabric cover 130. The slip-resistant material 150 may be a continuous or discontinuous layer. In this and other embodiments, slip-resistant material 150 may be composed of silicone or another biocompatible material(s), which provides a desired level of traction between fabric cover 130 and core 120 of prosthesis 110 by virtue of, for example, having a low durometer. Upon construction of prosthesis 110, fabric cover 130, and thus slip-resistant material 150, may be drawn tightly around core 120, for example, through the use of a stitch (not shown), which connects portions of cover 130 together. By tightening fabric cover 130 about core 120, in the way described above or otherwise, a secure contact between material 150 and core 120 may be established. In this manner, rotation between fabric cover 130 and core 120 may be retarded or prevented (e.g., via the friction established between slip-resistant material 150 and core 120), which may allow a user to suture cuff 140 to tissue within a patient without fabric cover 130 rotating or otherwise moving with respect to core 120. Likewise, once prosthesis 110 is secured in place within a patient, the user may be certain that prosthesis 110 will resist changing orientation, as core 120 will not rotate or otherwise move with respect to fabric cover 130.

In this and the other embodiments discussed below, slip-resistant material 150 may be relatively thin, and may be roughly between one one-thousandths (0.001) of an inch to one one-hundredth (0.010) of an inch in thickness. This ensures that the overall cross-sectional diameter of core 120 is not unnecessarily increased, which may result in a bulky and unmanageable prosthesis 110.

In an alternate embodiment, still referring to FIG. 3, slip-resistant material 150 may, instead of being formed on an interior surface 131 of fabric cover 130, be wrapped around all or a portion of the core 120 of prosthesis 110. In particular, slip-resistant material 150 may be configured as tubing and/or tape, which is formed of a biocompatible material (e.g., silicone) and is wrapped around core 120 to provide the same effect as the above-described embodiment. For example, slip-resistant material 150, in the form of tubing and/or tape, may be wrapped around core 120; and, once fabric cover 130 is secured tightly around core 120 of prosthesis 110, slip-resistant material 150 may prevent rotation of cover 130 with respect to core 120. Here, similar to the above-described embodiment, the tubing and/or tape, which forms slip-resistant material 150, may be relatively thin and may be anywhere between one one-thousandths (0.001) of an inch to one one-hundredth (0.010) of an inch in thickness.

In yet another embodiment, with continued reference to FIG. 3, prosthesis core 120 may be dip coated, sprayed, painted, or the like with a slip-resistant material 150, thus forming a slip-resistant layer 150 covering core 120. Before adhering slip-resistant material 150, in the form of a coating, spray, paint, or the like to core 120 of prosthesis 110, core 120 may also be treated so as to improve adherence between the slip-resistant material 150 and the core 120. In particular, core 120 may be mechanically roughed and/or plasma treated so as to aid in adhering slip-resistant material 150 to core 120 during coating, spraying, and/or painting.

In this embodiment, as with the other embodiments discussed above, the coating or layer of slip-resistant material 150 may provide a high level of friction between such material 150 and fabric 130 (e.g., once fabric 130 is secured tightly about core 120). Also, the thickness of slip-resistant material 150 may be minimal so as to add little to the bulk of prosthesis 110.

Referring now to FIGS. 5A-B, in an alternate method, a slip-resistant material 160 may be interposed between core 120 and fabric 130 through a thermal shrinking process. In particular, as shown in FIG. 5A, a tube of material 160 may be situated about the core 120 of prosthesis 110 (e.g., prior to securing fabric cover 130 thereto). The tube of material 160 may also have thermal-sensitive properties in that tube 160 may contract upon exposure to heat (or other thermal stimulus). Accordingly, the tube of material 160 may be situated in a first orientation (e.g., an expanded orientation) prior to heating, and may be situated in a second orientation (e.g., a collapsed orientation) after exposure to heat or other thermal stimulus. This contraction is exemplified by the disappearance of space 163 situated between slip-resistant material 160 and core 120, as shown in the transition between FIGS. 5A and 5B. Stated differently, after situating tube of material 160 about core 120 in an expanded orientation (FIG. 5A), heat or other thermal stimuli may be applied to such material 160 causing material 160 to collapse about core 120 in an amount according to space 163 (FIG. 5B). Thus, the tube of material 160 may be tightly drawn about core 120 through the application of heat (or other thermal stimulus) so as to preclude or lessen the tendency of fabric cover 130 to rotate with respect to core 120, that is, once cover 130 is tightly drawn about core 120 and material 160.

In a specific embodiment, tube 160 may also include an exterior surface 161 with a particularly tacky or high-friction surface. As such, once tube 160 is secured to core 120 via thermal shrinking, fabric cover 130 may be tightened about core 120 and tube 160 so as to prevent rotation and/or movement between core 120 and fabric cover 130. This may result in a prosthesis 110 having a core 120 with a slip-resistant tube 160 formed about the core 120, so as to provide friction between the core 120 and a fabric cover 130 secured about the core, as shown in detail in FIG. 5B.

In one embodiment, exterior surface 161 of tube 160 may also be provided with an adhesive material for adhering to fabric cover 130 and even further improving the anti-rotation feature(s) of prosthesis 110. Likewise, an interior surface 162 of tube of material 160 may include an adhesive material for more securely bonding to the surface of core 120 of prosthesis 110. As with the preceding embodiments, tube of material 160 may be composed of silicone or another biocompatible material(s) having a high coefficient of friction so as to prevent rotation between core 120 and fabric cover 130. Further, tube of material 160 may be relatively thin and may be anywhere from one one-thousandth (0.001) of an inch to one one-hundredth (0.010) of an inch in thickness, like in the preceding embodiments.

In yet other variants of the present invention, referring now to FIG. 2A, a biocompatible adhesive may be used to bond a portion or all of fabric cover 30 to core 20 of prosthesis 10. Alternatively, thermal or ultrasonic bonding may be used in the place of a biocompatible adhesive. For example, in the instance that fabric cover 30 is composed of multiple layers, as shown in FIGS. 2A-C, the initial or first layer of fabric cover may be secured, via a biocompatible adhesive or through thermal or ultrasonic bonding, to the core 20 of prosthesis 10. Then, subsequent layers of fabric cover 30 may be secured to core 20 via wrapping around and/or suturing to the initial layer of fabric, resulting a fabric covered core 20 having the anti-rotation features discussed above (e.g., the layers of fabric cover 30 may not rotate or otherwise move with respect to core 20).

In a particular embodiment, during thermal bonding, heat and pressure may be applied by clamping a heat source (not shown) about fabric cover 30 (or a layer thereof) and core 20, thus causing cover 30 (or a layer thereof) to bond to and conform to core 20. The same process may be used with ultrasonic bonding, except that high frequency waves may be used in the place of a traditional heat source. Stated differently, with ultrasonic bonding, high frequency waves may be used to generate friction between fabric cover 30 and core 20, thus causing cover (or a layer thereof) to secure to core 20. Accordingly, with these embodiments, a user may suture fabric cover 30, and therefore prosthesis 10, to a patient without movement resulting between cover 30 and core 20, as at least a portion of cover 30 may be secured or bonded to core 20.

Referring still to FIG. 2A, a further embodiment of the present invention may include a process in which an outer surface layer 21 of the core 20 may be mechanically altered in order to improve the frictional characteristics thereof. In particular, outer surface layer 21 of core 20 may be roughened up by sanding, sand blasting, carving vertical and/or horizontal notches into outer surface layer 21, or other like processes. In this way, once fabric cover 30 is secured to core 20, rotation and/or movement therebetween may be precluded or reduced, as fabric cover 30 may catch or engage with portions of the roughened outer surface layer 21.

Figure 7A:
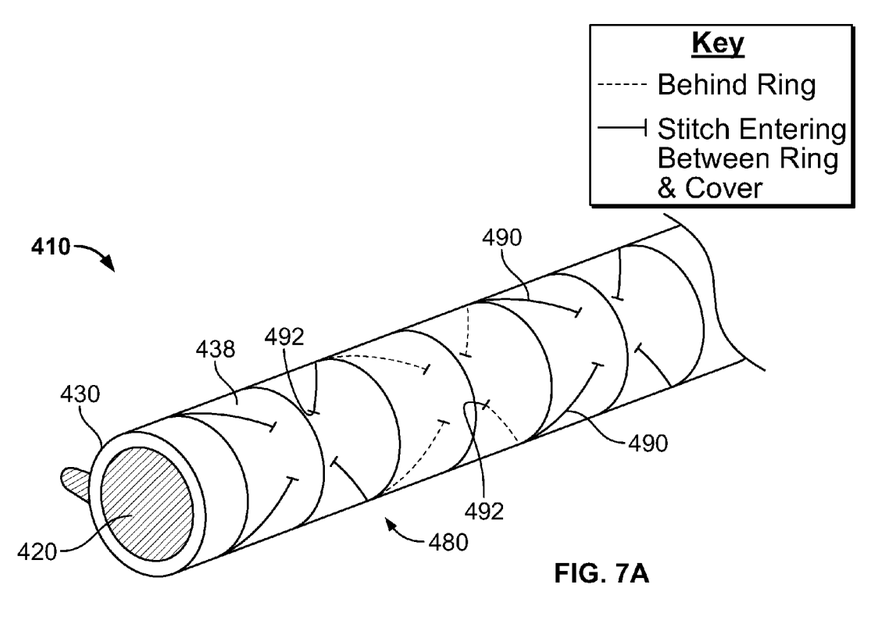
Figure 7B:
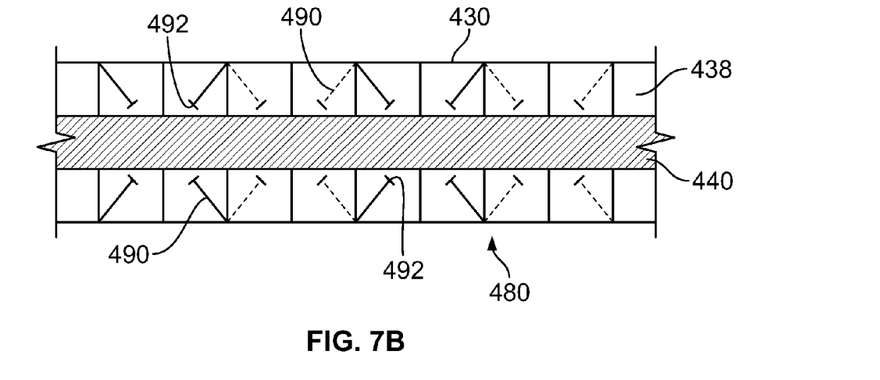
FIG. 7B is a side view of the prosthetic anatomical device with such a pattern.
Figure 7C:
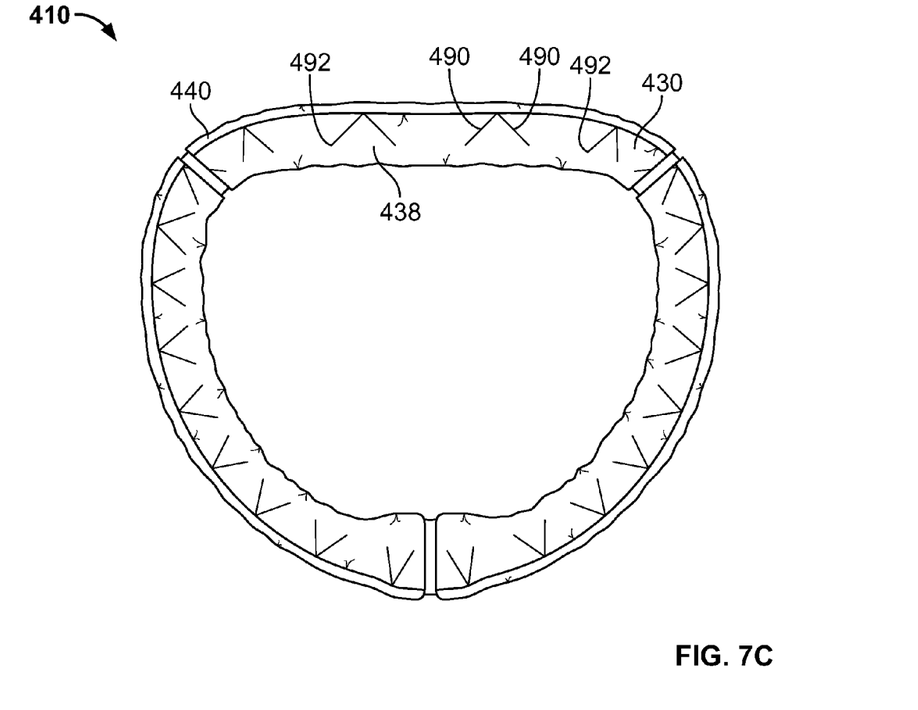
FIG. 7C is a top view of the prosthetic anatomical device of FIGS. 7A-B.

In the preceding embodiments, various methods and structures are described for reducing the tendency of a core of a prosthetic anatomical device (e.g., an annuloplasty ring) to slip or otherwise rotate with respect to a fabric cover surrounding the core. An alternate method for providing such anti-slip features is exemplified by a prosthesis 410, as shown in FIGS. 7A-C. Such prosthesis 410 includes a specially configured stitching pattern 480 for securing a core 420 of prosthesis 410 to a fabric cover 430 surrounding the core 420, and thereby providing anti-rotation functionality. As alluded to above, the particular stitching pattern 480 of FIGS. 7A-C, which is described in more detail below, may be used with any of the preceding embodiments (e.g., prostheses 10, 110, 210), or other known prostheses, to secure a fabric cover of such prosthesis to a core of the prosthesis.

As shown in FIG. 7A, which is a perspective view of prosthesis 410, the stitching pattern 480 on prosthesis 410 may form a cross-pattern along an outer surface 438 of cover 430. Such cross-pattern may be a series of sutures 490, which cross over one another at certain locations within the pattern 480. In particular, a set (or one or more) of sutures 490 may be wrapped around core 420 and fabric cover 430, with each suture 490 in the set traveling along certain portions of outer surface 438 of cover. Further, other sections of sutures 490 may extend between cover 430 and core 420, as shown. Stated differently, each suture 490 may, in one embodiment: (1) travel along outer surface 438 of cover 430 for a certain length; (2) be threaded through cover 430 (e.g., at positions 492) and travel between cover 430 and core 420 for a specified distance; and (3) then be threaded once again through cover 430 at positions 492 and travel a certain length along outer surface 438 of cover 430. This general pattern may also repeat itself for each suture 490, as shown in detail in FIG. 7A and particularly FIG. 7C. Sutures 490 may also be angled with respect to a longitudinal axis of core 420, such that a cross-stitch pattern 480 is formed. As noted by the key in FIGS. 7A-B, the pattern 480 may also be formed on both sides of prosthesis 410 (i.e., as shown in FIGS. 7A-B, the pattern 480 may extend in front of and behind the prosthesis 410 depicted). This is best depicted in FIG. 7C as well.

FIG. 7B illustrates a side view of prosthesis 410 in which cover 430 and a cuff 440 formed by cover 430 are visible. The cross-stitch pattern 480 of sutures 490, in this embodiment, may be such that each suture 490 of the pattern 480 crosses through the cover 430 and cuff 440 at position(s) 492. In other words, sutures 490 may extend fully through cuff 440 at positions 492 so as to secure cover 430 to core 420. Such is also shown in the top view of prosthesis 410 in FIG. 7C.

In use, the sutures 490 utilized to form pattern 480 may be cinched or pulled tight about cover 430 and core 420 to secure such cover 430 to core 420. This alone may prevent or mitigate rotation between cover 430 and core 420; and, with the optional addition of further anti-slip features as described in the preceding embodiments, rotation between cover 430 and core 420 of prostheses 410 (or the remainder of the prostheses 10, 110, 210) may be further retarded, or alternatively prevented altogether. Thus, cross-stitch pattern 480 of FIGS. 7A-C may, by itself or in combination with other features as discussed above, serve to mitigate rotation between core 420 and cover 430 of prosthesis 410. Accordingly, a user may be presented with a prosthesis 410 (or 10, 110, 210) that is easier to secure to the patient, and one that will not become dislodged or disoriented therefrom.

Prosthesis cores 20, 120, 220, 420 according to the above-described embodiments may be made from any suitable material, such as, for example, stainless steel, titanium, a ceramic, cobalt-chromium-nickel alloys, elgiloy, a shape-memory alloy, and/or a polymeric material, or a combination of any such materials. Further, sewing cuffs 40, 40', 140, 240, 440 may be formed from a soft fabric or material layer such as, for example, polyester, polytetrafluoroethylene (PTFE), or the like.

In the devices shown in the figures, particular structures are shown that are adapted to provide an improved sewing cuff and anti-rotation features therefor. The invention(s) also contemplates the use of any alternative structures for such purposes, including structures having different lengths, shapes, and configurations, as well as adjustable and non-adjustable prostheses. For example, although FIG. 1 shows a prosthesis 10 that is a complete, unbroken, generally D-shaped annulus, prosthesis 10 may have other shapes, and may alternatively be only a portion of an annulus (e.g., it may be C-shaped rather than D-shaped).

Further, with each of the preceding embodiments detailing the use of ant-slip features, it is contemplated that the material providing slip-resistance between the fabric cover 30, 130, 230, 430 and the core 20, 120, 220, 420 of prosthesis 10, 110, 210, 410 may not extend into the cuff 40, 140, 240, 440. In other words, cuff 40, 140, 240, 440 of fabric cover 30, 130, 230, 430 may be formed of a soft fabric material, as hereinbefore described, and may lack any other constituent material. As such, it may be relatively easy for a user to pass a needle and suture through cuff 40, 140, 240, 440, as no material and/or sub-structure will prevent its passage.

As another example, while FIG. 1 shows a sewing cuff 40 extending around the entire periphery of prosthesis 10, sewing cuff 40 may alternatively extend around only portions of prosthesis 10. This applies across the remainder of the embodiments discussed. Likewise, it is contemplated that the slip-resistant materials hereinbefore described may be situated along only portions between fabric cover 30, 30', 130, 230, 430 and core 20, 120, 220, 420. Thus, for example, using any of the methods discussed above, a slip-resistant material may be disposed between fabric cover 30, 30', 130, 230, 430 and core 20, 120, 220, 420 only at certain sections about core 20, 120, 220, 420 to thereby create a perforate layer of slip-resistant material.

In addition, while the slip-resistant materials of the aforementioned embodiments have been described as not extending into any portion of cuff 40, 40', 140, 240, 440 it is equally contemplated that such materials may, in some embodiments, extend into the cuff 40, 40', 140, 240, 440, if desired.

Although the invention(s) herein has been described with reference to particular embodiments, it is to be understood that these embodiments are merely illustrative of the principles and applications of the present invention(s). It is therefore to be understood that numerous modifications may be made to the illustrative embodiments and that other arrangements may be devised without departing from the spirit and scope of the present invention(s) as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic anatomical device comprising:
an annular core; and
a cover at least partially surrounding the core and forming a cuff extending radially outward from the core, the cover formed from a material layer having a first section folded at least once over itself and a second section folded at least once over itself, with a portion of the second section forming the cuff, wherein an inner layer of the first section of the cover is wrapped around the core.

2. The device of claim 1, wherein the second section is at least twice folded over itself.

3. The device of claim 2, wherein the first section is stitched to the second section, and a portion of the second section extends outward from the stitch to form the cuff.

4. The device of claim 3, wherein the cuff comprises at least three layers of material.

5. The device of claim 1, wherein portions of the cover are secured to the core, such that rotation between the portions of the cover and the core is precluded.

6. The device of claim 1, further comprising a polymer layer between the annular core and the cover, whereby rotation between the cover and the core is reduced.

7. The device of claim 1, wherein the annular core comprises an annuloplasty ring.

8. The device of claim 1, wherein at least a portion of the second section of the cover is wrapped around the core.

9. The device of claim 1, wherein the first section of the cover comprises at least a partial loop, and a stitch connects the first and second sections of the cover through the partial loop.

10. The device of claim 9, wherein the partial loop is connected to the second section of the cover at a spaced distance from an end of the cuff.

11. The device of claim 1, wherein the core does not extend into the cuff.

12. The device of claim 1, wherein an inner layer of the first section of the cover is bonded to the core.

13. A prosthetic anatomical device comprising:
an annular core with an outer surface;
a cover at least partially contacting the outer surface of the core and having at least one section forming a cuff for suturing the cover to tissue within a patient, the cuff extending radially outward from the core; and
means for mitigating movement of the annular core relative to the cover.

14. The device of claim 13, wherein the movement mitigating means includes a roughened up outer surface on the annular core sufficient to increase friction between the core and the cover, the cover contacting the roughened up outer surface, such that relative movement between the cover and core is mitigated.

15. The device of claim 14, wherein the outer surface of the annular core is sanded, sand blasted, or formed with notches.

16. The device of claim 13, wherein the core has an elongated member having an outer surface and a transverse cross-section, the transverse cross-section defining a perimeter, and wherein the movement mitigating means includes a stitch pattern formed into the cover about the cross-sectional perimeter of the elongated member, the stitch pattern securing the cover relative to the core.

17. The device of claim 16, wherein the stitch pattern comprises at least two sutures extending cross-wise with respect to one another and being arranged between the cover and the outer surface of the elongated member.

18. The device of claim 16, wherein the stitch pattern comprises at least two sutures extending cross-wise with respect to one another, each suture extending through a portion of the cuff.

19. The device of claim 13, wherein the cover comprises multiple layers and the movement mitigating means includes a first layer of the cover being thermally or ultrasonically bonded to the outer surface of the annular core, or bonded to the outer surface of the annular core via an adhesive.

20. The device of claim 13, wherein the annular core comprises an annuloplasty ring.

21. The device of claim 13, wherein the cover comprises multiple layers and the movement mitigating means includes a first layer of the cover being bonded to the outer surface of the annular core.

22. The device of claim 21, wherein a portion of the cuff is stitched to a separate section of the cover.

23. The device of claim 13, wherein the core does not extend into the cuff.

24. A prosthetic anatomical device comprising:
an annular core with an outer surface;
a cover at least partially surrounding the core and having at least one section forming a cuff for suturing the cover to tissue within a patient, the cuff extending radially outward from the core; and
a slip-resistant material situated between the core and the cover to mitigate relative movement between the cover and the core, the slip-resistant material being configured to contract from an expanded position spaced apart from the core to a contracted position abutting the core.

25. The device of claim 24, wherein the slip-resistant material is operable to contract from its expanded position to its contracted position in response to a thermal stimulus.

26. The device of claim 24, wherein the slip-resistant material is a biocompatible material approximately one one-thousandth of an inch to one one-hundredth of an inch in thickness.

27. The device of claim 24, wherein the slip-resistant material has exterior and interior surfaces, at least one of which is bonded to an inside surface of the cover or the outer surface of the annular core, respectively.

28. The device of claim 24, wherein the slip-resistant material does not extend into the cuff.

29. The device of claim 24, wherein an outer surface of the slip-resistant material has a coefficient of friction sufficient to mitigate relative movement between the cover and the slip-resistant material.

30. The device of claim 24, wherein the outer surface of the core is roughened.

31. The device of claim 24, wherein the annular core comprises an annuloplasty ring.

* * * * *